United States Patent [19]

Gemmill, Jr. et al.

[11] Patent Number: 5,395,831
[45] Date of Patent: Mar. 7, 1995

[54] TREATING CARDIAC DISORDERS WITH Δ9(11)-DEHYDRO-8-ISOESTRONE

[75] Inventors: Frederick O. Gemmill, Jr.; Chester E. Orzech, both of Rouses Point, N.Y.; Steven J. Adelman, Doylestown, Pa.

[73] Assignee: American Home Products Corporation, Madison, N.J.

[21] Appl. No.: 224,849

[22] Filed: Apr. 8, 1994

[51] Int. Cl.6 .............................................. C07J 1/00
[52] U.S. Cl. .................................... 514/179; 552/625
[58] Field of Search ......................... 514/179; 552/625

[56] References Cited

U.S. PATENT DOCUMENTS

| | | | |
|---|---|---|---|
| 3,394,153 | 7/1968 | Re | 260/397.45 |
| 3,542,819 | 11/1970 | Marshall . | |
| 3,649,621 | 3/1972 | Stein et al. | 260/239.55 |
| 3,689,512 | 9/1972 | Shah et al. | 260/397.4 |
| 4,357,278 | 11/1982 | Quinkert et al. . | |
| 5,210,081 | 5/1993 | Raveendranath et al. | 514/179 |
| 5,288,717 | 2/1994 | Raveendranath et al. | 514/179 |

OTHER PUBLICATIONS

Budavari, S. et al., The Merck Index, 11:570 (1989) 3582.
Magerlein, B. J. et al., American Chem. Society 80:2220 (1953).
Weiske, R., Chemical Abstracts 61:1478h (1964).
Collins, D. J. et al., Australian Journal of Chemistry 36:339 (1983).
Subbiah, R. M. T. et al., Journal of Clinical Endocrinology Mebabolism 77:1095 (1993).

Primary Examiner—Johann Richter
Assistant Examiner—Kimberly J. Kestler
Attorney, Agent, or Firm—Arnold S. Milowsky

[57] ABSTRACT

This invention relates to 8α-3-hydroxyestra- 1,3,5(10),9(11)tetraen-17-one (Δ9(11)-dehydro-8-isoestrone) (VI),

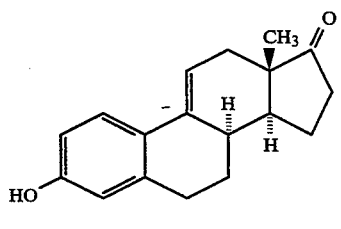

Δ9(11)-Dehydro-8-isoestrone(VI)

to the process for its preparation, to pharmaceutical compositions containing said 8α-3-hydroxyestra-1,3,5(10), 9(11)tetraen-17-one (Δ9(11)-dehydro-8-isoestrone) (VI) and to the use of said 8α-3-hydroxyestra-1,3,5(10),9(11)tetraen-17-one (Δ9(11)-dehydro-8-isoestrone) (VI) for modifying the balance between bone production and bone resorption, and as an antioxidant in a host animal, including man.

2 Claims, No Drawings

TREATING CARDIAC DISORDERS WITH Δ9(11)-DEHYDRO-8-ISOESTRONE

This invention relates to 8α-3-hydroxyestra-1,3,5(10),9(11)tetraen-17-one (Δ9(11)-dehydro-8-isoestrone) (VI), to the process for its preparation, to pharmaceutical compositions containing said 8α-3-hydroxyestra-1,3,5(10),9(11)tetraen-17-one (Δ9(11)-dehydro-8-isoestrone) (VI) and to the use of said 8α-3-hydroxyestra-1,3,5( 10),9(11)tetraen-17-one (Δ9(11)-dehydro-8-isoestrone) (VI) for modifying the balance between bone production and bone resorption and as an antioxidant in a host animal, including man.

BACKGROUND OF THE INVENTION

Osteoporosis is a skeletal disorder which is evidenced by a decrease in bone density throughout the body. In fact, both the bone mineral (calcium phosphate called "hydroxyapatite") and the bone matrix (major protein called "collagen") are slowly lost. This condition may begin to occur in humans as early as age 30. In general, the process is more rapid in postmenopausal women than in men. However, after age 80 there is no sex difference in the incidence of osteoporosis. In the course of 10 to 20 years of bone loss there may be symptoms of back pain and X-ray evidence of deformation of the spine. At older ages, the brittleness of the bones becomes evident by the ease with which the proximal femur ("hip") fractures. Osteoporosis is the most common cause of fractures in people over age 45.

Although the cause of osteoporosis is poorly understood, it is believed that there is an imbalance between bone production and bone resorption (bone breakdown). Bone remains a dynamic tissue throughout the life of an animal. That is, new bone is continuously being formed and old bone is continuously being resorbed. However, in animals suffering from an osteoporotic condition, net bone resorption exceeds bone formation.

A survey indicates that in the United States there may be fifteen to twenty million people afflicted with osteoporosis [W. A. Peck (Chairman), NIH Osteoporosis Consensus Conference, J. Am. Med. Assoc., 252:799-802 (1984)]. Various types of osteoporosis are designated according to special conditions believed to be causative: senile (aging); post-menopausal (female loss of estrogenesis); disuse (chronic immobilization); steroid (long term steroid treatment as in arthritis). Osteoporosis may also be manifested in dental problems since the mandible appears to lose mass more rapidly than any other bone. Thus, periodontal disease involving a loosening of the adult teeth may be an early sign of osteoporosis.

The mechanism of bone loss is at present poorly understood. Moreover, the present methods of treatment are generally unsatisfactory. These include anabolic agents, various drugs containing phosphorous, Vitamin D, calcium salts, fluorides and calcitonin.

Estrogen replacement therapy has been the therapy of choice for osteoporosis in post-menopausal women.

Physical therapy is another method currently used to treat osteoporosis since immobilization can cause osteoporosis at any age. Thus, many physicians believe that exercise and physical therapy can prevent the progression of the disease in elderly patients. However, physical therapy can be harmful for patients with fractures and, moreover, overstrenuous exercise can cause fractures in patients with severe osteoporosis.

Other treatments include the administration of a fluoride salt such as sodium fluoride which has been shown to promote bone growth clinically, apparently by stimulating collagen synthesis. However, a serious side effect is poorly calcified, irregular bone growth. Another treatment involves infusion of calcium and Vitamin D to counteract the deficiency of calcium or impaired absorption of calcium which is symptomatic in some elderly patients. There is, however, no evidence that a higher intake of calcium will prevent osteoporosis or increase bone mass in adults.

The most promising therapeutic approach to the treatment of osteoporosis is the administration of agents which have been designed to modify the balance between the rate of bone production and the rate of bone resorption in such a manner that the ratio of the former to the latter is increased, resulting in no net bone loss. After the previously occurred bone losses have been restored, a steady state is reached where the rate of bone production and rate of bone resorption are equal. Such a modification may be effected by stimulating the physiological mechanism of bone deposition, i.e., bone formation, or by retarding the mechanism of bone resorption, or both. Drugs presently in use or in the experimental stages for accomplishing these purposes include phosphonates, calcitonin and mithramycin. However, all of these drugs suffer serious drawbacks.

Mithramycin, an antibiotic, has anti-tumor activity together with hypocalcemic activity, causing a reduction of serum calcium which in turn is believed to be indicative of a decrease in the relative rate of bone resorption—i.e., bone resorption relative to bone production. Side effects, however, include renal and hepatic toxicity as well as nausea. Likewise, the organic phosphonates have side effects which include extraskeletal calcification, hypotension and renal failure. Calcitonin presents an immunological problem because it is commonly derived from a non-human source. Thus, none of the foregoing agents are at present suitable for use alone in the treatment of osteoporosis.

PRIOR ART

The prior art relates to equilin itself Budavari S (1989). *The Merck Index* 11th ed. Merck & Co Inc, Rahway, New Jersey, p. 3582 and to another known equilin isomer, 3-hydroxyestra-1,3,5(10),9(11)-tetraen-17-one (D9(11)-dehydroestrone) (II) disclosed in Magerlein B. J., Hogg J. A. (1958). Preparation and reactions of 11-substituted 1,3,5(10)-estratrienes. I. 11-Oxygenated estrones and estradiols. *J Am Chem Soc* 2220-2225.

Schering A-G (by Weiske R) (1964). Ger Offen 1,177,636. *Chem Abstr* 61:14748h.

Collins DJ, Sjövall J (1983). The structure and function of oestrogens. IV. Synthesis of 17α-ethynyloestradiol specifically polydeuterated in ring C. *Aust J Chem* 36:339-360.

SUMMARY OF THE INVENTION

DESCRIPTION OF THE INVENTION

This invention relates to the compound of formula (VI)

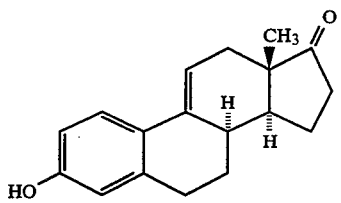

Δ9(11)-Dehydro-8-isoestrone(VI)

or a pharmaceutically acceptable salt thereof.

The compound of the present invention (VI) is a double bond isomer of equilin represented by the formula (III)

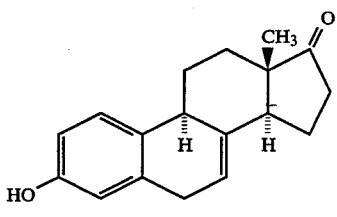

EQULIN (III)
(Δ7-Dehydroestrone)

and is prepared from equilin by treatment with a strong acid in an aprotic media. The compound of the present invention (VI) is useful for 1) the treatment or prevention of estrogen deficiency induced bone loss
2) reducing cardiovascular plaque formation leading to decreased mortality
3) symptomatic relief of postmenopausal estrogen deficiency including but, not limited to, vasomotor hot flashes, depression and insomnia.
4) prevention of urinary incontinence.
5) treatment of periodontal disease
6) as an antioxidant.

It is also another object of this invention to provide a method whereby a host animal, including man, suffering from osteoporosis is treated in order to modify the balance between the rates of bone deposition and bone resorption in said host animal whereby the ratio of the latter to the former is reduced.

Still another object of this invention is to provide a process for the treatment of a host animal in order to prevent the deterioration of existing healthy bone tissues in said host animal. It is possible that these agents could also be of utility in the treatment of hypercalcemia of malignancy, Paget's disease, and the arthritides.

It is a further object of this invention to provide a process for the treatment of periodontal disease.

It is yet another object of this invention to use the compound of the present invention (VI) as an antioxidant.

DETAILED DESCRIPTION OF THE INVENTION

The compound of formula (VI) of this invention is used alone or in combination with pharmacologically acceptable carriers, the proportion of which is determined by the solubility and chemical nature of the compound, chosen route of administration and standard medical practice. For example, they are administered orally in the form of capsules, tablets, suspensions or solutions or they may be injected parenterally. Capsules and tablets are the preferred mode of administration. For parenteral administration they can be used in the form of a sterile solution containing other solutes, for example enough saline or glucose to make the solution isotonic.

The capsule and tablet compositions contain the active ingredient in admixture with non-toxic pharmaceutical excipients known to be suitable in the manufacture of capsules and tablets. Suitable pharmaceutical excipients are, for example, starch, milk sugar, certain types of clay and so forth. The tablets can be uncoated or they can be coated by known techniques so as to delay disintegration and absorption in the gastrointestinal tract and thereby provide a sustained action over a longer period.

The aqueous suspensions of the compounds of formula (VI) contain the active ingredient in admixture with one or more non-toxic pharmaceutical excipients known to be suitable in the manufacture of aqueous suspensions. Suitable excipients are, for example, methylcellulose, sodium alginate, gum acacia, lecithin and so forth. The aqueous suspensions can also contain one or more preservatives, one or more coloring agents, one or more flavoring agents and one or more sweetening agents.

Non-aqueous suspensions can be formulated by suspending the active ingredient in a vegetable oil for example, arachis oil, olive oil, sesame oil, or coconut oil, or in mineral oil, for example liquid paraffin, and the suspension may contain a thickening agent, for example beeswax, hard paraffin or cetyl alcohol. These compositions can also contain a sweetening agent, flavoring agent and antioxidant.

The dosage of the compound of formula (VI) will vary with the form of administration, and the particular compound chosen. Furthermore, it will vary with the particular host as well as the age, weight and condition of the host under treatment, as well as with the nature and extent of the symptoms. Generally, treatment is initiated with small dosages substantially less than the optimum dose of the compound. Thereafter, the dosage is increased by small increments until the optimum effect under the circumstances is reached. In general, the compounds of this invention are most desirably administered at a concentration level that will generally afford effective results without causing any harmful or deleterious side effects. For example, the effective amount of the compounds for oral administration can usually range from about 200 mg to 1200 mg/day in single or divided doses although, as aforementioned, variations will occur. However, a dosage level that is in the range of from about 500 mg to 900 mg/day in single or divided doses is employed most desirably for oral administration in order to achieve effective results. 8a-3-hydroxyestra- 1,3,5(10),9(11)tetraen- 17-one (D9(11)-dehydro-8-isoestrone) (VI) would be administered to humans at a daily dose of 200 mg to 1200 mg.

The following examples are provided to illustrate the methods of preparation and testing of the compound of the present invention. These examples are not meant to be considered, in any way, as limitations of the breadth and scope of the present invention. The temperatures expressed in these examples are in degrees centigrade.

EXAMPLE 1

General Methods

Melting points (mp) were taken using a Thomas-Hoover Capillary Melting Point apparatus and are uncorrected. Specific rotations [a]$_D$ were obtained with a Perkin-Elmer model 241 polarimeter and a microcell at room temperature. Concentrations were about 1% in dioxane unless otherwise noted. Ultraviolet (UV) spectra were obtained with a Hewlett Packard model 8452 dime array spectrophotometer in USP alcohol. Infrared (IR) spectra were obtained using KBr pellets with a Nicolet 20DX FTIR spectrometer. $^1$H nuclear magnetic resonance (NMR) spectra were obtained with a Bruker AM 400 spectrometer in deuterochloroform unless otherwise noted and are reported as parts per million downfield from tetramethyl silane. Mass spectra (MS) were obtained using a Finnigan-MAT model 8230 double focusing magnetic sector instrument or a Hewlett Packard model 5995 single quadripole instrument with electron impact ionization.

Preparation of
3-Hydroxyestra-1,3,5(10),8(9)-tetraen-17-one
(Δ8(9)-Dehydroestrone) (I)

To a stirred polyethylene reaction vessel (500 mL) containing 125 mL of liquid hydrogen fluoride at −50° C. was added 5 g (18.7 mmoles) of equilin (III). The mixture was stirred at −50° C. for 24 hours and then poured into 2 L of ice water. The resulting solid was filtered, washed with water, and dried in a vacuum over P$_2$O$_5$. The crude product (4.8 g, 96% yield) was, by gas chromatography (using the procedure of The United States Pharmacopeia 22nd ed. suppl 1 (1990). Mack, Easton, Pennsylvania, p 127.) 90% 3-hydroxyestra-1,3,5(10),8(9)-tetraen-17-one (I) and 10% of another product (VI). Recrystallization from hot benzene-hexane (1:1) failed to remove (VI). The crude mixture (500 mg) was chromatographed in two portions on a Sephedex ® LH-20 column (5×50 cm packed to a height of 47 cm) and eluted with cyclohexane/benzene/methanol (500:150:75) (using the procedure of Krol G. J., Masserano R. P., Carney J. F., Kho B. T. (1970). Quantitative separation of free estrogens by liquid partition chromatography. J Pharm Sci 59:1483–1487). The flow rate was 4 mL/min and the eluent was monitored at 270 nm. Several fractions were collected and analyzed by gas chromatography. The fraction containing (I) eluted at approximately 2350 mL. Fractions of like composition and purity were combined and evaporated to dryness to give 350 mg of (I) free of the other product (VI). This chromatographed material was further purified by dissolving in hot benzene, then hexane was added to the cloud point. The solution was allowed to cool to room temperature and then kept at 4° C. for 24 hours. The product was filtered, air dried, and dissolved in hot ethanol. Charcoal was added to the hot solution, followed by filtration, and addition of hot water to the cloud point. After cooling to room temperature and then 4° C. for 60 hours, it was filtered and air dried to give 300 mg of pure (I), mp 229°–230° C. with decomposition (purple color before melting). See Table 1 for spectral and other data.

The fractions containing product (VI) were saved for further work-up.

Preparation of
3-Hydroxyestra-1,3,5(10),9(11)-tetraen-17-one
(Δ9(11)-Dehydroestrone) (II)

To a stirred polyethylene reaction vessel (500 mL) containing 150 mL of liquid hydrogen fluoride at 0° C. was added 6 g (22.4 mmoles) of equilin (III). The mixture was stirred at 0° C. for 0.5 hours, a 50 mL portion was removed, and poured into 1 L of ice water. The resulting solid was filtered., washed with water, and dried under vacuum over P$_2$O$_5$. Gas chromatography (using the procedure of The United States Pharmacopeia 22nd ed. suppl 1 (1990). Mack, Easton, Pa. p 2127.) of the crude product showed 3 components: 38% 3-hydroxyestra-1,3,5(10),9(11)-tetraen-17-one (II) , 55% 3-hydroxyestra-1,3,5(10),8(9)-tetraen-17-one (I), and 7% of the same product, (VI), as from the synthesis of (I). The remaining reaction mixture was stirred at 0° C. for another hour and a second 50 mL portion was removed. This was worked up as above and showed by gas chromatography the same 3 components in the ratio of 55% 3-hydroxyestra-1,3,5(10),9(11 )-tetraen-17-one (II), 40% 3-hydroxyestra-1,3,5(10),8(9)-tetraen-17-one (I), and 5% of the same product, (VI), as from the synthesis of (I). The remaining 50 mL mixture was stirred for another 2 hours at 0° C. and the reaction mixture was worked up as above. Gas chromatography showed that the crude product was 100% 3-hydroxyestra-1,3,5(10),9(11 )-tetraen-17-one (II). This material (1.6 g, 80% yield) was dissolved in 60 mL of boiling methanol-/acetone (2:1) and charcoal added. The solution was filtered hot to remove the charcoal and 10 mL of distilled water added to the boiling solution. The solution was allowed to cool to room temperature and then at 4° C. for 48 hours. The product was filtered and air dried to give 1.2 g of pure 3-hydroxyestra-1,3,5(10),9(11 )-tetraen-17-one (II), mp 255°–257° C. with decomposition. See Table 1 for spectral and other data.

Preparation of
8α-3-Hydroxyestra-1,3,5(10),9(11)-tetraen-17-one
(Δ9(11)-Dehydro-8-isoestrone) (VI)

The fractions containing (VI) from the synthesis of (I) were combined and rechromatographed using the same column and eluting solvent. Fractions were collected and checked by gas chromatography. Pure fractions of (VI) were combined, evaporated to dryness, and recrystallized from ethanol/water to give 120 mg, mp 243.5°–244.5° C. with decomposition. See Table 1 for spectral and other data.

Results and discussion

Jacquesy (see Jacquesy J. C., Joly G, Gesson J. P. (1972). Reactions in hyperacidic media. Selective isomerization of equilin in acidic or hyperacidic media. Compt rend Acad 274:969–971.) stated that at 0° C. (II)

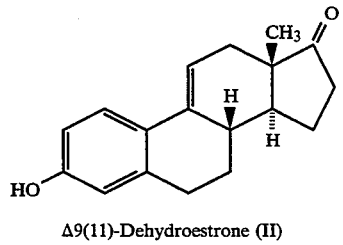

Δ9(11)-Dehydroestrone (II)

was the only product and that at −30° C. (I) was the only product. Due to equipment restraints synthesis of (I) was carried out at −50° C. Analysis of the −50° C. crude reaction product indicated a ratio of 9:1 of (I) to the unknown, (VI), which was neither starting material, (II), nor (IV). Further, if the 0° C. reaction was stopped before completion, various ratios of (I) to (II) to (VI)

were found. Compound (VI) was separated by liquid partition chromatography on a large Sephedex®LH-20 column (by the procedure of Krol G. J., Masserano R. P., Carney J. F., Kho B. T. (1970). Quantitative separation of free estrogens by liquid partition chromatography. *J Pharm Sci* 59:1483-7). Analysis of (VI) by mass spectrometry, IR, UV and ¹H NMR led to the conclusion that it was an isomer of equilin. Based on Jacquesy's theoretical treatment of the isomerization reaction, (VI) was thought to be 3-hydroxyestra-1,3,5(10),8(14)-tetraen-17-one (Δ8(14)-dehydroestrone) (V).

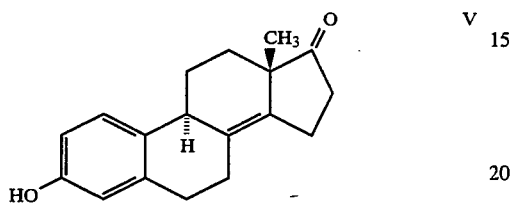

V

However, the nuclear magnetic resonance spectrum of (VI) showed a one proton multiplet at 6.00 ppm δ (CDCl₃) indicative of a vinyl proton. In addition, the ¹H NMR spectrum of (VI) is similar to that of (II). Both have a one vinyl proton multiplet near 6 ppm δ (CDCl₃) and similar aromatic splitting patterns. The aromatic splitting pattern for (I) is considerably different from that of (VI). Since an 8-14 double bond isomer has no vinyl protons, (V) was ruled out in favor of a 9-11 double bond isomer with opposite orientation of the proton at the 8 and/or 14 positions with respect to (II) (see structures (VI), (VII), and (VIII) for the 9(11) double bond isomers which vary in the 8 and 14 positions only).

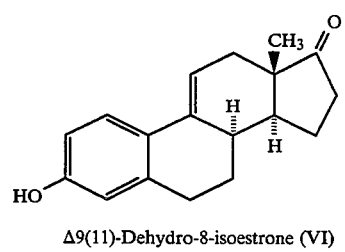

Δ9(11)-Dehydro-8-isoestrone (VI)

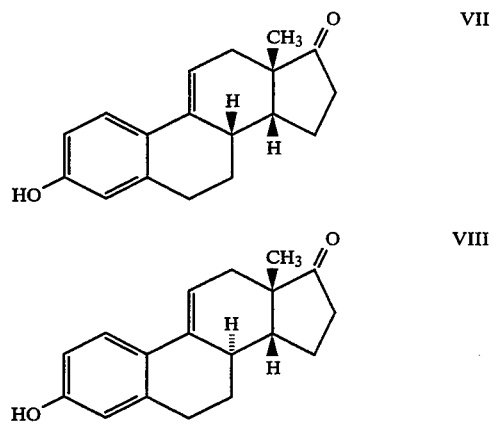

As a further indication that the double bond is in the 9-11 position, the UV spectrum of (VI) is quite similar to that of (II).

High field 1H NMR studies have shown that (VI) reverts spontaneously to (I) in chloroform solution indicating that the 14-proton is alpha as in all the other estrogenic steroids and that it is the 8-proton which has reversed. On this basis we have assigned it the structure of 8α-3-hydroxyestra-1,3,5(10),9(11)-tetraen-17-one (Δ9(11)-dehydro-8-isoestrone) (VI).

Analytical and spectral data for (VI) as well as equilin and equilin isomers (I), (II), and (IV) are presented in Table 1.

TABLE 1

| Compound | mp (C.) | $[\alpha]^{RT}$ (degrees) | MS m/e | IR (KBr) $\nu(cm^{-1})$ |
|---|---|---|---|---|
| EQUILIN (III) (Δ7-Dehydroestrone) | 237-239 238-240[10] | +308 +308[10] | 268 (M+) | 1719 (C=O) 1615 (arom) |
| Δ6-Dehydroestrone (IV) | 265-269 261-263[11] 265-266[12] | -129 -127[11] | 268 (M+) | 1714, 1725 (C=O) 1615 (arom) |

TABLE 1-continued

| Structure | mp (°C) | [α] | MS | IR (cm⁻¹) |
|---|---|---|---|---|
| Δ8(9)-Dehydroestrone (I) | 229–230<br>228–230[13] | +40.7<br>+86[13,b] | 268 (M+) | 1717 (C=O)<br>1607 (arom) |
| Δ9(11)-Dehydroestrone (II) | 255–257<br>257–259[14] | +295<br>+297.5<br>+299[b]<br>+301[16,b] | 268 (M+) | 1721 (C=O)<br>1606 (arom) |
| Δ9(11)-Dehydro-8-isoestrone (VI) | 243.5–244.5 | +182 | 268 (M+) | 1719 (C=O)<br>1607 (arom) |

[a]Ethanol

[b]Chloroform

| Compound | UV (nm) λmax | ε | $^1$H NMR (CDCl$_3$/TMS) δ (ppm) |
|---|---|---|---|
| EQUILIN (III)<br>(Δ7-Dehydroestrone) | 281<br>282 | 1977<br>2291[17,a] | 0.79(s, 3H, 18-CH$_3$), 5.52(m, 1H, 7-H), 6.60(d, 1H, 4-H), 6.70(dd, 1H, 2-H), 7.26(d, 1H, 1-H) |
| Δ6-Dehydroestrone (IV) | 304<br>271<br>262<br>221<br>304<br>262<br>220 | 2522<br>6096<br>7477<br>25731<br>2754[11,a]<br>8913[11,a]<br>30903[11,a] | 0.81(s, 3H, 18-CH$_3$), 6.04(dd, 1H, 7-H), 6.46(dd, 1H, 6-H), 6.52(d, 1H, 4-H), 6.57(dd, 1H, 2-H), 7.01(d, 1H, 1-H)[b] |
| Δ8(9)-Dehydroestrone (I) | 279<br>214<br>275 | 15565<br>17229<br>15900[3,a] | 0.90(s, 3H, 18-CH$_3$) 6.64(s, 3/2H, 2-H, 3-H), 6.66(D, ½H, 2-H), 7.09(d, 1H, 1-H) |

TABLE 1-continued

| Structure | | | | |
|---|---|---|---|---|
| 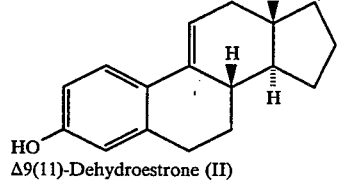  Δ9(11)-Dehydroestrone (II) | 289<br>263<br>298<br>263.5 | 3334<br>17913<br>3138[16,a]<br>18073[16,a] | 0.94(s, 3H, 18-CH₃), 6.13(m, 1H, 11-H), 6.57(d, 1H, 4-H), 6.65(dd, 1H, 2-H), 7.49(d, 1H, 1-H) | |
| 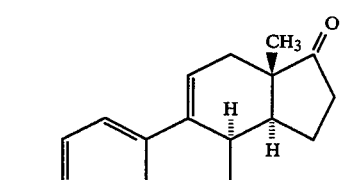  Δ9(11)-Dehydro-8-isoestrone (VI) | 295<br>260 | 2580<br>16943 | 0.97(s, 3H, 18-CH₃), 6.00(m, 1H, 11-H), 6.58(d, 1H, 4-H), 6.65(dd, 1H, 2-H), 7.40(d, 1H, 1-H) | |

[a]Ethanol;
[b]DMSO-d₆

References

10. Budavari S (1989). *The Merck Index* 11th ed. Merck & Co Inc, Rahway, New Jersey, p. 3582.
11. Kaufmann St, Pataki J, Rosenkranz G, Romo J, Djerassi C (1950). Steroids VI. The Wohl-Ziegler bromination of steroidal 1,4-dien-3ones. Partial synthesis of 6-dehydroestrone and equilenin. *J Am Chem Soc* 72:4531-4534.
12. Pearlman W. H., Wintersteiner O (1940). Estrogens with oxygen in ring B. II. Δ6-Isoequilin from 7-hydroxyestrone. *J Biol Chem* 132:605-612.
13. Banes D, Carol J (1953). The constituents of isoequilin A. *J Biol Chem* 204:509-515.
14. Magerlein B. J., Hogg J. A. (1958). Preparation and reactions of 11-substituted 1,3,5(10)-estratrienes. I. 11-Oxygenated estrones and estradiols. *J Am Chem Soc* 80:2220-2225.
15. Schering A-G (by Weiske R) (1964). Ger Offen 1,177,636. *Chem Abstr* 61:14748h.
16. Collins DJ, Sjövall J (1983). The structure and function of oestrogens. IV. Synthesis of 17α-ethynyloestradiol specifically polydeuterated in ring C. *Aust J Chem* 36:339-360.
17. Zderic J. A., Carpio H, Bowers A, Djerassi C (1963). Steroids CCXXVIII. The synthesis of equilin. *Steroids* 1:233-249.

The useful osteoporotic activity of the compound of formula (VI) are demonstrated by standard pharmacological tests, for example, the test designated: Bone Resorption Assay: $^{45}$Ca Release from Rat Limb Bones.

The purpose of this assay is to identify compounds that inhibit basal or stimulated bone resorption in culture.

The ability of 8α-3-hydroxyestra-1,3,5(10),9(11)tetraen-17-one (Δ9(11)-dehydro-8-isoestrone) (VI) to modify the process of bone resorption can be evaluated essentially as described by L. G. Raisz, Bone resorption in tissue culture. Factors influencing the response to parathyroid hormone. (J. Clin. Invest. 44:103-116, 1965) and P. H. Stern et al, Comparisons of fetal rat limb bones and neonatal mouse calvaria: Effects of parathyroid hormone and 1,25-dihydroxyvitamin D₃ (Calcif. Tissue Int. 172-176, 1983).

PROCEDURE

Limb bone preparation.

Timed pregnant Sprague-Dawley CD® rats (Charles River) are administered 100 μCi $^{45}$CaCl₂ (NEN calcium —45 NEZ-013) in 100 μl of 0.9% saline, subcutaneously, on day 18 of gestation. The rats are sacrificed the following day by CO₂ asphyxiation. The fetuses are removed and the fight forelimbs excised and placed in a Petri dish containing ice cold explant medium consisting of modified BGJ$_b$-Fitton Jackson media (custom formulation, Gibco No. 78-0088) adjusted to pH 7.3 to which 10 mM TES is added. The modified BGJ$_b$ media is obtained without salts, glucose or bicarbonate and is supplemented before use with 0.1 mM MgCl₂, 1.25 mM CaCl₂, 5.3 mM KCl, 0.7 mM MgSO₄, 130 mM NaCl, 1.0 mM NaH₂PO₄, 1 g/L glucose, 50 mg/L Na acetate and 100 U/mL penicillin G. The medium is sterilized by passage through a 0.2 μM filter (Nalge). Under a dissecting microscope, the bones are gently cleaned of adherent tissue and the cartilaginous ends removed.

Incubation and drug treatment

The midshafts are placed, individually, on 3×3 mm squares of filter paper (Gelman GN-6 metricel filters; 0.45 μM pore size) which rest on stainless steel screens in wells of 24-well culture plates containing 0.5 mL of preincubation medium. The preincubation medium is brought to 37° C. prior to transfer of bones. The preincubation medium consists of the modified BGJ$_b$ medium (with salts and glucose as above), pH 7.3, containing 29 mM NaHCO₃. After incubation for 18-24 hours at 37° C. in 5% CO₂, the bones are transferred on their screen/filter paper supports to new plates containing, in a total volume of 0.5 mL/well at 37° C., the test compound diluted in preincubation medium supplemented with 15% heat inactivated horse serum (Gibco No. 230-6050), pH 7.3, with or without a bone resorption stimulating agent (e.g. parathyroid hormone [PTH] or interleukin-1 [IL-1]). For compounds that require nonaqueous solvents, dilutions are made from the appropriate stock solution with medium. In these instances, basal and bone resorption stimulated controls exposed to an equivalent concentration of the vehicle are included.

An additional group of bones that have been subjected to boiling for 1 hour (kill control) are used to establish background, non cell mediated, exchange of $^{45}Ca$. The fight ulna and radius from each fetus are used. Both bones are subjected to the same treatment and each treatment group consists of bones from 4 or more fetuses. Treatments are randomly assigned using a preclinical statistics program (PS-ALLOC). After a 48 hour incubation at 370° C. in 5% $CO_2$, the bones are removed from the medium and extracted in 0.5 mL of 0.1N HCl for 1 or more days. Duplicate 150 μL aliquots of the incubation medium and the bone extract are analyzed for $^{45}Ca$ radioactivity in 5 mL of liquid scintillation cocktail.

CALCULATIONS;

The percentage of bone $^{45}Ca$ released into the medium is determined as follows:

$$\frac{^{45}Ca\ CPM\ in\ medium}{^{45}Ca\ CPM\ in\ medium + ^{45}Ca\ CPM\ in\ bone} \times 100$$

Results are normally expressed as the ratio of the percent $^{45}Ca$ release of the experimental group versus the appropriate vehicle control.

The useful osteoporotic activity of the compound of formula (VI) can be further demonstrated by the test designated: Basal Bone Resorption Assay: $^{45}Ca$ Release from Rat Limb Bones.

The purpose of this assay is to test stimulators and inhibitors of bone resorption in vitro. The release of $^{45}Ca$ from in vitro labeled murine bone explants into the culture media is taken as an index of bone resorption.

Bone labelling procedure.

Rat pups are labelled in vitro by injecting pregnant dams (18 days) with 100 μCi of $^{45}Ca$.

Explant preparation.

Two days after the initiation of labelling, the dam is anesthetized with halothane and killed by cervical dislocation. The pups are ablated and quickly decapitated. The calvaria (frontal and parietal bones), forelimbs (containing radii and ulnae), and hind limbs (tibiae) are removed and placed in control media in a petri dish. Bones are debrided of soft tissue by a combination of blunt dissection, and gentle rolling on bibulous paper, taking care not to disturb the periosteum. Cartilaginous ends are cut off long bones. Calvaria are cut in half along midline suture. Bones are separated into 3 categories: calvaria halves, tibiae and ulnae/radii. Groups of eight (per bone group) are randomly placed in 24-well culture plates containing 0.5 mL of control media. Cultures are maintained at 37° C. in a humidified incubator of 95% air: 5%$CO_2$.

These bones are incubated for 24 hours, media is aspirated from the bones and replaced with fresh media containing test substances. Each bone group has a control group of 8 and a dead bone group of 8. The devitalized cultures are obtained by heating the bones in medium at 55° C. for 60 minutes. The bones are incubated at 37° C. for an additional 72 hours. At the end of this period a 100 microliter aliquot of media is removed and placed in a scintillation vial. Ten mL of Aquasol is added, the $^{45}Ca$ is quantified in a scintillation spectrometer. Bones are rinsed in saline, placed in a scintillation vial, hydrolyzed overnight in 0.75 mL 6N HCl at room temperature. The hydrolyzed bone solution is neutralized by the addition of 2.25 mL of 2N NaOH, followed by 10 mL of Aquasol, the $^{45}Ca$ content is determined by scintillation spectrometry.

Analysis $^{45}Ca$ release into culture medium from the 24–96 hour period is individually compared to $^{45}Ca$ release in control cultures and to devitalized bone via Dunnett's test.

The useful osteoporotic activity of the compound of formula (VI) can be further demonstrated by the test designated: Denervation Induced Osteopenia in Rats.

The purpose of this assay is to evaluate the effect, in rats, of agents on the reduction in bone mass (osteopenia) induced by immobilization resulting from surgical severance (denervation) of the sciatic nerve.

Female, Sprague Dawley CD ® rats, ovariectomized or intact, weighing 225 to 250 g, obtained from Charles River are used.

The animals are housed in plastic cages (4 or 5 rats/cage) with food (rat Purina 500 Chow) and water ad libitum; 14/10 day/night cycle.

After one week of in-house acclimatization, the animals are randomly divided into groups of 6 to 10 rats/group. Each rat is weighed, anesthetized with an intraperitoneal administration of 100 mg/kg ketamine (Bristol Laboratories, Syracuse, NY) and 0.75 mg/kg Acepromazine (Aveco, Ft. Dodge IA). The left hind limb is shaved and denervated by making a lateral incision parallel to the femur and by surgically removing half of a centimeter of the sciatic nerve adjacent to caudofemoralis and adductor brevis muscles. The incision is closed with wound clips. After surgery, the rats are housed in cages with absorbent bedding to minimize additional trauma to the immobilized limb. A 24 hour post-surgery recovery period is allowed before the initiation of the drug treatment.

The concentration of the drug stock is calculated to be delivered in a volume of 0.1 mL/100 gram body weight. The drug solution or a uniform suspension is prepared in 1% Tween 80 in normal saline. The drugs are administered via oral or parenteral routes daily (five times a week) for four weeks.

A sequential triple labeling of mineralized tissue is employed to determine the osseous changes (especially the bone formation) and the mineralization rates. Each animal is administered 90 mg/kg Xylenol orange (Fisher Scientific Company), S.C., 15 mg/kg Calcein (Sigma Chemical Company), S.C. and 15 mg/kg Demeclocycline (Sigma Chemical Company), i.p., approximately 21 days, 10 days and 2 days prior to the termination of the study, respectively.

At the end of the fourth week, each rat is weighed, anesthetized with an intraperitoneal administration of 100 mg/kg ketamine with 0.75 mg/kg Acepromazine and approximately 4 mL of blood collected via cardiac puncture. The anesthetized rats are euthanized by exposure to carbon dioxide. The femora and tibiae from both limbs are dissected free of soft tissue.

(i) Femora are ashed at ~1100° C. for 16 hours using a muffle furnace.—(ii) Proximal tibia are fixed, dehydrated and embedded undecalcified in a methyl methacrylate-glycol methacrylate mixture. Longitudinal tissue sections (10 microns) are prepared on a Polycut S microtome (Reichert). Staining is performed on free-floating sections using a modified Goldner's stain, which are then mounted and coverslipped.

Cancellous bone content in the proximal tibia is quantified (as two dimensional bone mineral area [B.Ar]) with an image analysis processing device (software developed by Drexel University).

The areas of the tibia selected for cancellous bone content evaluation are the primary and secondary spongiosa. To select and standardize this area for evaluation, the epiphyseal growth plate-metaphyseal junction is oriented parallel to the abscissa of the digitizing screen. Bone elements 1.7 mm (secondary spongiosa) and 0.2 mm (primary spongiosa) from the growth plate and equidistant from the flanking conical elements are then quantified as described above. The total area evaluated is 2.30 mm wide and 1.45 mm deep, constituting a 3.34 mm² area.

Body weight, femur mass (dried or ashed) and trabecular (cancellous) bone mineral area (B.Ar) are determined.

The difference (both absolute and percent change) in femur mass and bone mineral area between intact (control) and denervated limbs of a treatment group are compared with that for the vehicle group using a one-way analysis of variance with Dunnett's test, or other multiple comparison methods.

Bone is degraded during the process of bone resorption and this leads to the subsequent development of osteoporosis. The present invention provides a method for the treatment of a host animal in order to modify the balance between the rate of bone resorption and the rate of bone deposition in said host animal whereby the ratio of said rate of bone resorption to said rate of bone deposition is reduced, comprising administering to said host animal an amount, sufficient to modify said balance and reduce said ratio, of 8α-3-hydroxyestra-1,3,5(10),9(11)tetraen-17-one (Δ9(11)-dehydro-8-isoestrone (VI).

The administration of 8α-3-hydroxyestra-1,3,5(10),9(11)tetraen-17-one (Δ9(11)-dehydro-8-isoestrone) (VI) in accordance with this invention can be supplemental to other regimens for the treatment of osteoporosis or periodontitis. For example, the administration of 8α-3-hydroxyestra-1,3,5(10),9(11)tetraen-17-one (Δ9(11)-dehydro-8-isoestrone) (VI) can be supplemental to the 600 mg to 1200 mg daily intake of calcium as calcium phosphate or calcium carbonate. Also, the administration of 8α-3-hydroxyestra-1,3,5(10),9(11)tetraen-17-one (Δ9(11)-dehydro-8-isoestrone) (VI) can be supplemental to estrogen replacement therapy such as 0.625 mg daily of conjugated equine estrogen.

The compound of this invention (VI) is also useful as an antioxidant. By virtue of this utility, the compound (VI) can be used to treat, inhibit, or ameliorate atherosclerosis, coronary artery disease, cardiovascular disease, restenosis (particularly resulting from a balloon catheter angioplasty procedure), skin aging and wrinkling, and Alzheimer's disease. By virtue of its antioxidant properties, the compound of this invention (VI) is also useful as in the treatment of carcinomas. By virtue of its antioxiant properties, the compound of this invention (VI) is also useful for preventing free radical generation and is thereby useful in the prophylaxis and retardation of cellular damage caused by free radicals.

We claim:

1. A method of treating atherosclerosis in a mammal which comprises administering an effective amount of Δ9(11)-dehydro-8-isoestrone to said mammal.

2. A method of treating coronary artery disease in a mammal which comprises administering an effective amount of a Δ9(11)-dehydro-8-isoestrone to said mammal.

* * * * *